United States Patent [19]
Roger

[11] Patent Number: 5,171,277
[45] Date of Patent: Dec. 15, 1992

[54] METHOD AND APPARATUS FOR REMOVING PROSTHETIC CEMENT

[76] Inventor: Gregory J. Roger, 5 Kent Street, Collaroy, New South Wales, Australia, 2097

[21] Appl. No.: 646,618
[22] PCT Filed: Jul. 28, 1989
[86] PCT No.: PCT/AU89/00319
   § 371 Date: Jan. 29, 1991
   § 102(e) Date: Jan. 29, 1991
[87] PCT Pub. No.: WO90/01299
   PCT Pub. Date: Feb. 22, 1990

[30] Foreign Application Priority Data
   Jul. 29, 1988 [AU] Australia .................. PI9580

[51] Int. Cl.⁵ .............................................. A61F 2/28
[52] U.S. Cl. ........................................ 623/16; 606/96; 606/80
[58] Field of Search .................. 623/16, 18, 20, 23; 606/96, 80

[56] References Cited

U.S. PATENT DOCUMENTS

4,222,382  9/1980  Antonsson et al. .
4,781,181 11/1988  Tanguy ............................. 606/80

FOREIGN PATENT DOCUMENTS

17673/83  3/1984  Australia .
095296   11/1983  European Pat. Off. .
121142   10/1984  European Pat. Off. .
121780   10/1984  European Pat. Off. .
3522649   1/1986  Fed. Rep. of Germany .
87/02571  5/1987  World Int. Prop. O. .

*Primary Examiner*—David Isabella
*Attorney, Agent, or Firm*—Fleit, Jacobson, Cohn, Price, Holman & Stern

[57] ABSTRACT

A process for removal of cement from the medullary canal of a patient's long bone comprising: determining the profile of a line of intersection of a plane, and a cement/bone interface intersected by that plane; determining the thickness of the cement in the plane; forming a substantially planar cutting blade with a cutting edge having a profile corresponding to the profile of the line; inserting the cutting blade into the cavity with the blade lying in the plane, the cutting edge directed towards the interface, and to a depth such that corresponding points of the cutting edge are adjacent corresponding points on the line causing the cutting blade to reciprocate; inserting into the cavity a guide member to urge the blade into the cement towards the cement/bone interface; removing the cement from the cavity.

10 Claims, 6 Drawing Sheets

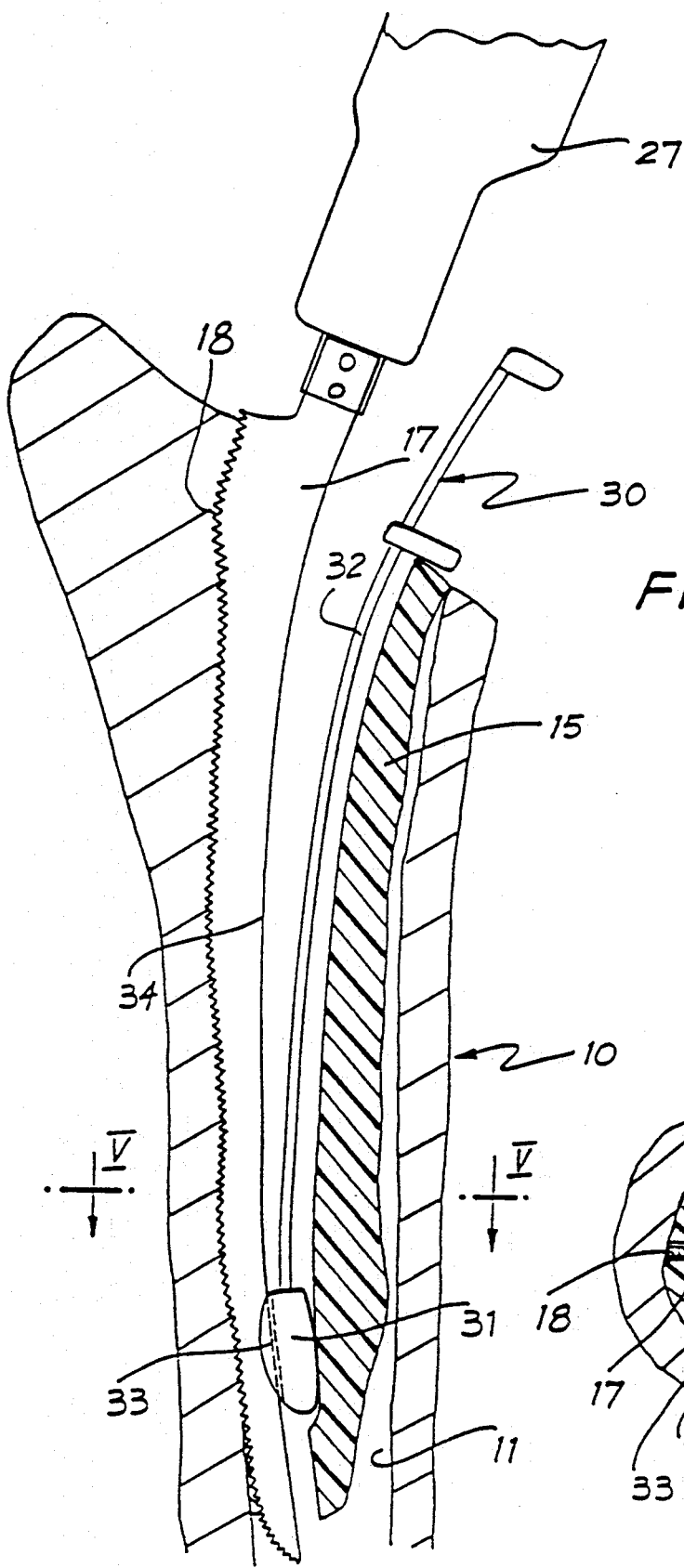
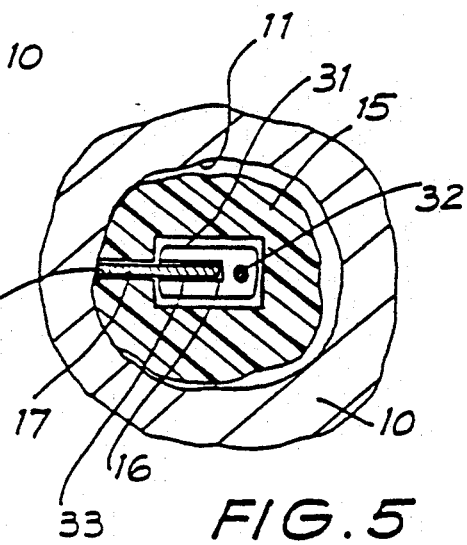
FIG. 4
FIG. 5

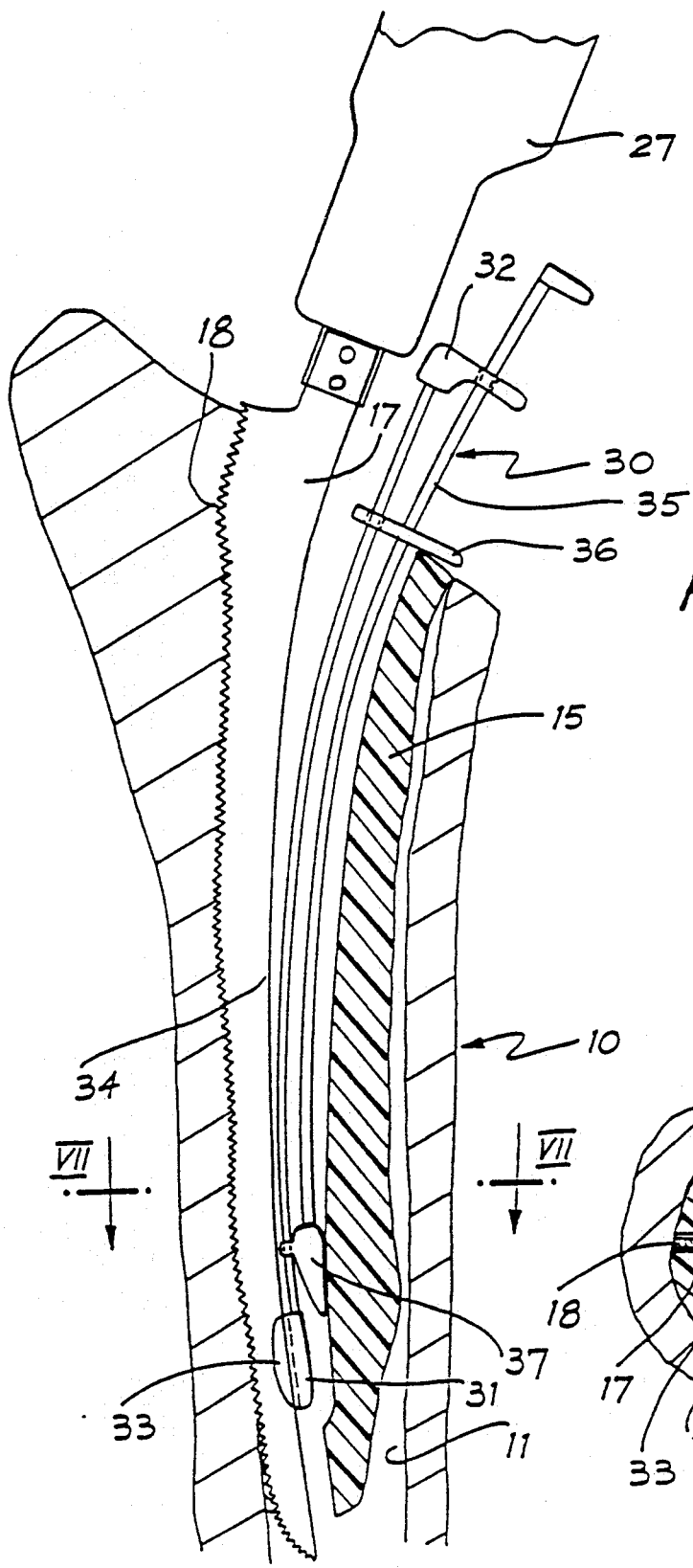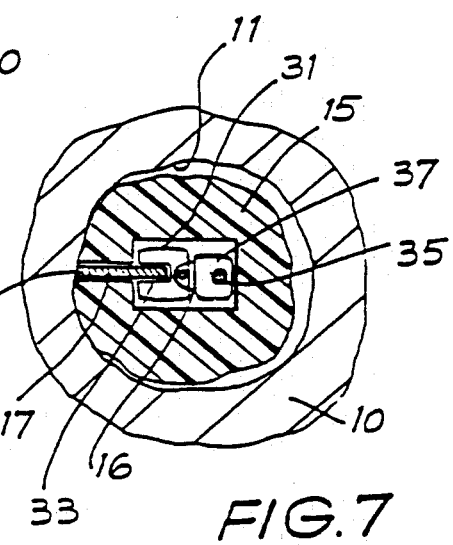
FIG. 6
FIG. 7

METHOD AND APPARATUS FOR REMOVING PROSTHETIC CEMENT

TECHNICAL FIELD

The present invention relates to an improved process for the removal of prosthetic cement from the medullary canal of a patient's long bone during the replacement of a joint prosthesis, and to a cutting blade for use therein.

BACKGROUND ART

The present inventor has proposed in PCT patent application PCT/AU86/00321 that the removal of prosthetic cement from the medullary canal of a patient's long bone can be facilitated during a joint prosthesis replacement operation by making two or more longitudinally extending cuts through the bone cement after removal of the old prosthesis. These cuts divide the originally tubular bone cement into a number of segments which may be conveniently levered away from the associated bone and removed from the medullary canal. In the aforementioned patent application means were described for forming such cuts through the prosthetic cement substantially without cutting into the underlying bone. These means included guide means to guide a saw blade along the line of intersection of a longitudinal plane extending through the bone, the prosthetic cement and a prosthetic cavity therein and a bone/prosthetic cement interface intersected by the plane.

The present inventor has also discovered that these guide means may be dispensed with if a cutting blade with a suitably profiled cutting edge is provided with depth limiting means which can bear against the surface of the prosthetic cavity adjacent the said plane to limit the depth to which the blade can cut into the prosthetic cement along the plane to the depth of the prosthetic cement along that plane (see PCT/AU88/00019).

It has been now found by the inventor that there may be some difficulty in forming appropriate depth limiting means on the blade and that if such means are formed on the blade that the blade is then dedicated to a single cut on a single patient and cannot be reused. It has also been found that as the blade is quite long but necessarily quite thin there may be difficulty in applying sufficient cutting pressure to the blade adjacent its tip to effectively cut through the full depth of the cement.

DISCLOSURE OF THE INVENTION

The present invention thus consists in a process for the removal of prosthetic cement from the medullary canal of a patients long bone during replacement of a joint prosthesis, comprising the steps of:

a) determining the profile of a line of intersection of a plane, which extends longitudinally through the bone, the prosthetic cement and a prosthetic cavity therein, and a cement/bone interface intersected by that plane, b) determining the thickness of the prosthetic cement in the said plane at least at selected points along the said bone, c) forming or selecting a substantially planar cutting blade with a cutting edge having a profile substantially corresponding to the profile of the line, d) inserting the cutting blade into the prosthetic cavity with the blade lying in the said plane, the cutting edge directed towards the said cement/bone interface, and to a depth such that corresponding points on the cutting edge are adjacent corresponding points on the said line, e) causing the cutting blade to reciprocate, f) inserting into the prosthetic cavity between a non-cutting edge of the blade and a wall of the prosthetic cavity spaced from the said cement/bone interface a guide member adapted to urge the cutting edge of the blade into the prosthetic cement towards the said cement/bone interface but substantially not beyond it, g) repeating steps (e) to (f) to form at least one other cut through the prosthetic cement, and h) removing the segments of prosthetic cement so formed from the medullary canal.

In another aspect the present invention consists in a kit of parts for use in the removal of prosthetic cement from the medullary canal of a patient's long bone during the replacement of a joint prosthesis, the kit of parts comprising i) at least one substantially planar blade having a cutting edge, the cutting edge having a profile substantially corresponding to the profile of the line of intersection of a plane, which extends longitudinally through the long bone, the prosthetic cement and a prosthetic cavity therein, and a cement/bone interface intersected by that plane, and ii) at least one guide member adapted to be inserted into the prosthetic cavity between a non-cutting edge of the blade and a wall of the prosthetic cavity spaced from the said cement/bone interface and adapted to urge the cutting edge of the blade into the prosthetic cement towards the said cement/bone interface but substantially not beyond it.

The blade is preferably elongate having a front cutting edge, carrying an array of cutting teeth, and a back edge which is smooth.

The guide member preferably comprises a wedge-shaped member at the end of an elongate handle. The wedge-shaped member having a front face and a back face and being formed on its front face with a slot extending along its length, parallel to the handle. The slot being such that the back edge of the blade may slidably fit into it. If the guide member is slid down the prosthetic cavity with the slot of the wedge-shaped member in registry with the back of the blade and the back face of the wedge-shaped member bearing against the wall of the prosthetic cavity then the blade will be urged to cut into the adjacent cement to a depth dependent upon the total cutting depth of the blade and the maximum thickness of the wedge less the depth of the slot. If the maximum thickness of the wedge less the depth of the slot are selected so that the distal end of the blade is urged into the cement the correct amount when the wedge is inserted into the cavity a given depth then the surgeon carrying out the procedure can ensure that he cuts the correct depth into the cement merely by sliding the wedge down the cavity and thereby forcing the distal end of the blade into the cement to the correct depth. The upper or proximal part of the blade may be then urged into the cement and the depth cut judged by eye.

Accordingly, in a preferred embodiment of the present invention the total cutting depth of the blade plus the maximum thickness of the wedge less the depth of the slot is equal to the distance from the wall of the prosthetic cavity spaced from the cement/bone interfaces to the cement/bone interface. It is more preferred that the maximum thickness of the wedge is equal to the diameter of the cavity at a point approaching the distal end of the cavity and that the total cutting depth of the blade less the depth of the slot is equal to the depth of cement at that point.

In one preferred embodiment of the invention the guide member comprises a wedge as described above but of a width less than that required to force the blade into the cement to the correct depth. In this embodiment the guide member also includes a further wedge slidable on the handle of the first wedge and adapted to be pushed into the cavity to urge the first wedge into contact with the back of the blade and thus the blade to cut into the cement.

In a preferred embodiment of the present invention the process for the removal of prosthetic cement from the medullary canal of a patient's long bone includes the step of boring a hole in the prosthetic cement at the blind end of the prosthetic cavity prior to step (d). It is preferred that this hole is made with a drill and a distal drill guide, the distal drill guide comprising a tapered tube adapted to fit within the prosthetic cavity adjacent the blind end thereof and around the drill when the drill is inserted into the prosthetic cavity.

In a further preferred embodiment a proximal drill guide is provided at the proximal end of the prosthetic cavity, said proximal drill guide comprising a tunnel through which the drill passes, the tunnel being connected to a handle mounted at 90° to the longitudinal axis of the tunnel.

In a preferred embodiment of the present invention the kit of parts includes the distal drill guide described above, and more preferably also includes the proximal drill guide described above.

It is preferable that at least three and more preferably four cuts are made through the prosthetic cement. The cuts are preferably equiangularly disposed around the cavity.

The process and the cutting blade according to this invention are particularly suitable for use in replacement hip prosthetic operations in which an old prosthesis is removed from the femur and replaced with a new prosthesis.

BRIEF DESCRIPTION OF THE DRAWINGS

FIG. 4 is a vertical sectional view through the femur of FIG. 3 with a reciprocating saw blade in position after having made a saw cut through the prosthetic cement using a first embodiment of the guide member.

FIG. 5 is a transverse sectional view along V—V of FIG. 4.

FIG. 6 is a vertical sectional view through the femur of FIG. 3 with a reciprocating saw blade in position after having made a saw cut through the prosthetic cement using another embodiment of the guide member.

FIG. 7 is a transverse sectional view along VII—VII of FIG. 6.

BEST MODE OF CARRYING OUT THE INVENTION

Figure 1:
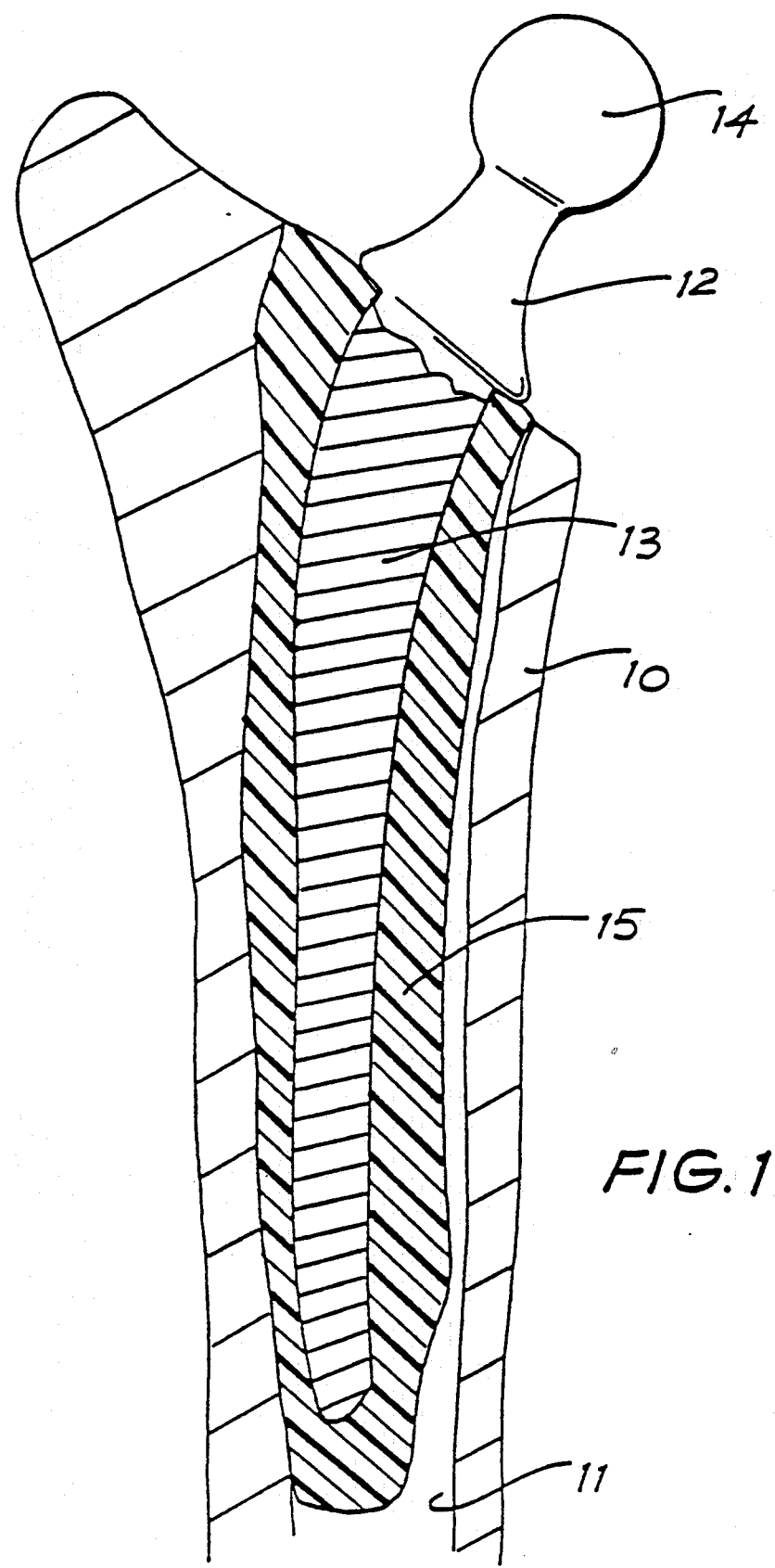
FIG. 1 is a vertical sectional view through a femur into which an artificial hip prosthesis has been fixed.

The invention is hereinafter described for the replacement of the femural part of a total hip replacement prosthesis with reference to the drawings hereinbefore identified.

The femur 10 of a patient has in the medullary canal 11 a hip prosthesis 12 comprising a stem 13 and head 14. The prosthesis 12 was originally firmly held in place in the medullary canal 11 by prosthetic cement 15 comprising polymethyl methacrylate. Over time the prosthesis 12 and the cement 15 have worked loose in the medullary canal 11 of the femur 10.

The hip prosthesis 12 can usually be easily removed from the cement 15 by pulling the prosthesis 12 longitudinally of the bone. The withdrawn stem 13 leaves a cavity 16 in the cement 15. The problem then remains of how to remove the cement 15 without damaging the bone 10.

In the process according to this invention the patient is, prior to removal of the old prosthesis, examined using X-rays or a CT scanner. If X-ray examination is used one X-ray photograph is taken from the front and one from the side of the patient to define the geometry of the stem 13 relative to the bone 10 along two defined planes and thus the configuration of the cement 15 along these same planes. The CT examination can also provide this information.

Figure 2:
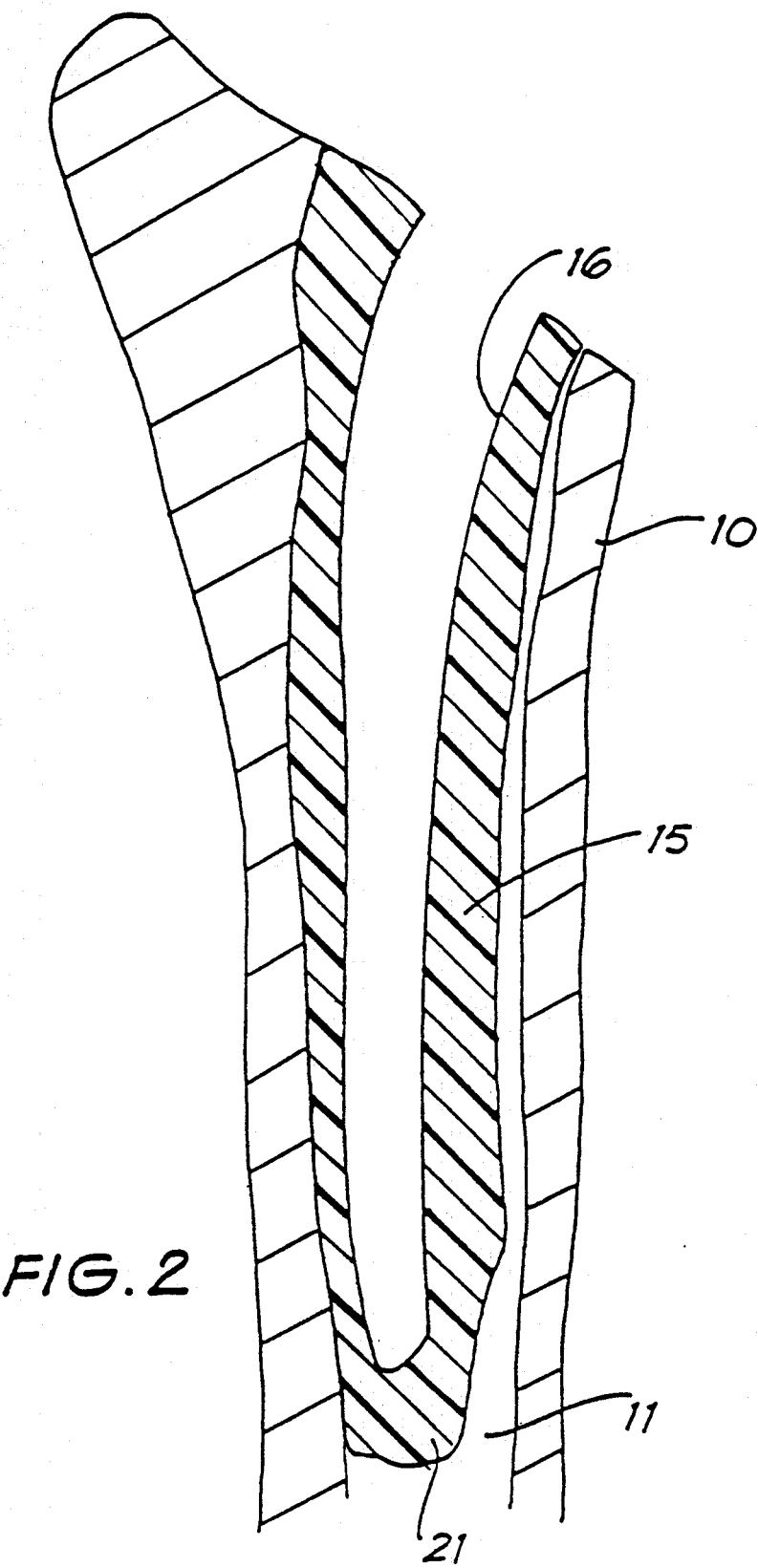
FIG. 2 is a vertical sectional view through the femur of FIG. 1 with the prosthesis removed and showing by cross hatching an area of the prosthetic cement to be removed by sawing.

The thickness of the cement 15 is measured along the above planes by examination of the X-ray photographs or CT scan. The thickness of one cut through cement 15 is shown by cross-hatching in FIG. 2. Appropriate jig saw blades 17 can then be made each having a cutting edge profile 18 corresponding to the profile of the cement 15 bone 10 interface along one of the defined planes.

The saw blades 17 are preferably formed using standard saw making techniques. The blade blanks will generally be formed in a mass produced fashion and then teeth cut and set in the usual way for industry. It is preferred that the teeth are maximally set to give the least cutting heat when operating in bone cement. If desired computer aided design (CAD) software may be used to transform the X-ray images or the CT scan directly into instructions for the production of customised saws.

Figure 3:
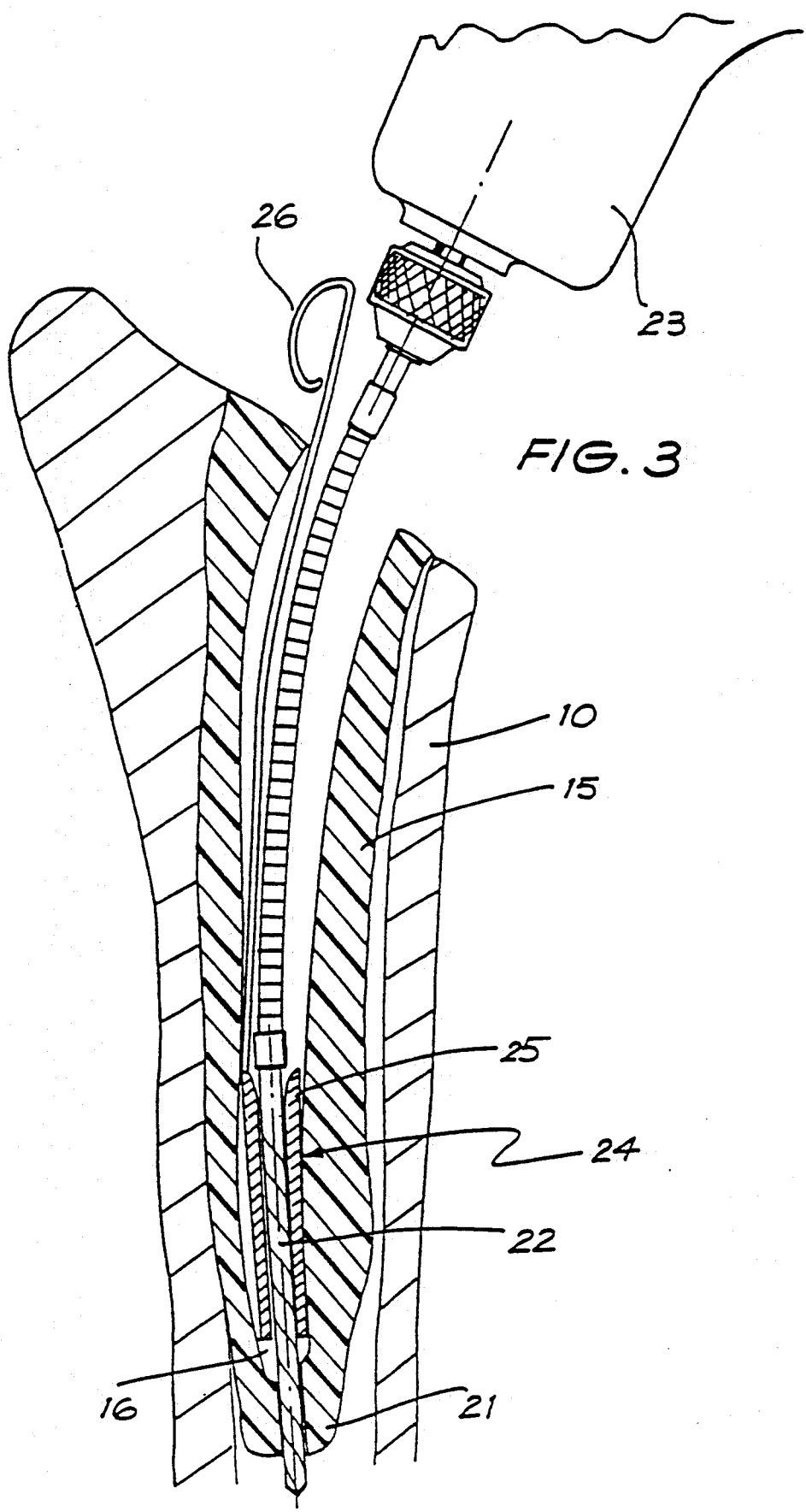
FIG. 3 is a vertical sectional view through the femur of FIG. 2 showing the base of the prosthetic cement being drilled out.
Figure 8:
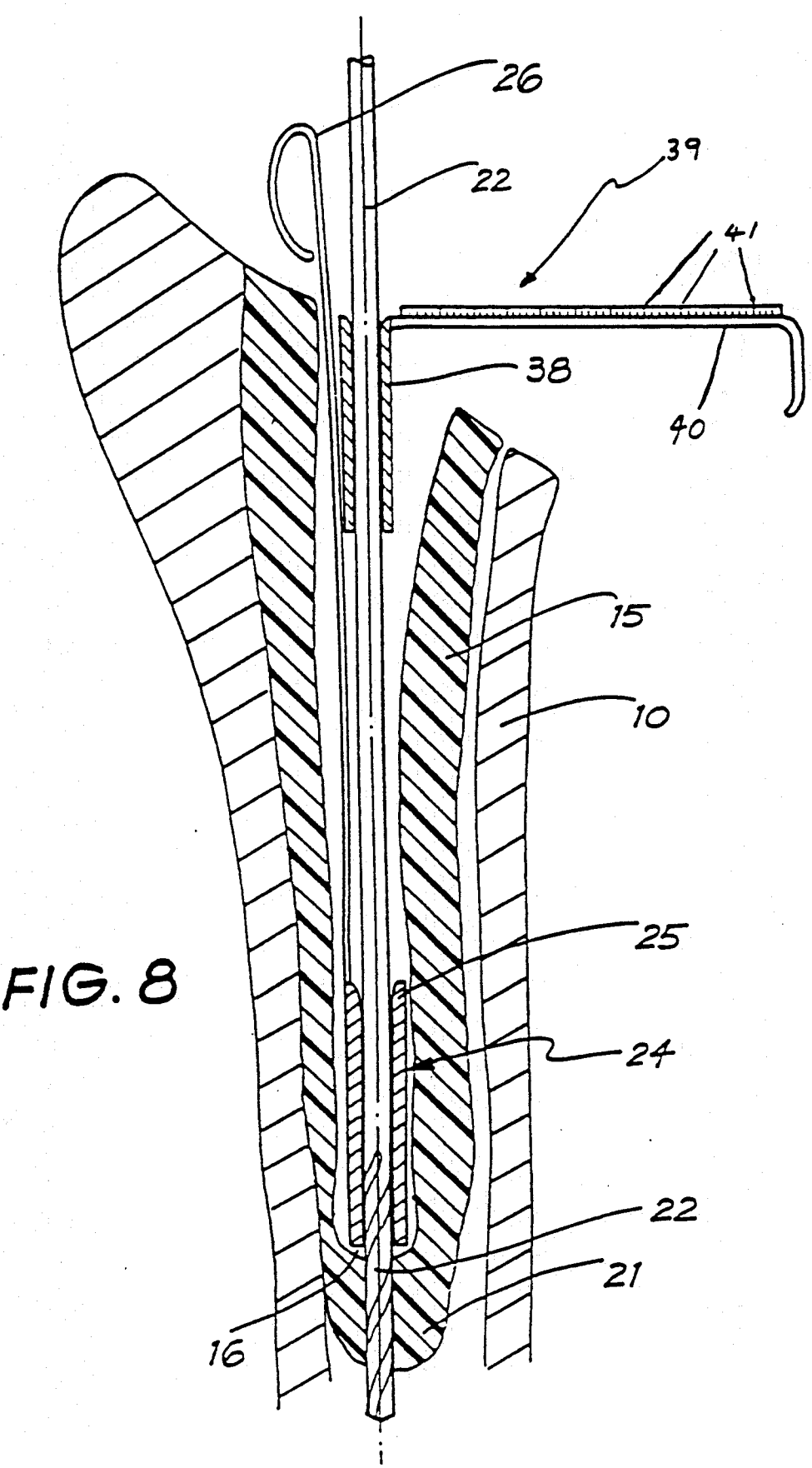
FIG. 8 is a vertical sectional view through the femur showing the positioning of the drill used to drill out the base of the prosthetic cement.

Once the old prosthesis 12 has been withdrawn from the femur 10 a hole is drilled in the blind end 21 of the prosthetic cement 15 using a drill bit 22 driven by an electric or pneumatic drill 23 and guided by a distal drill guide 24. The drill bit 22 may be flexible as shown in FIG. 3 or rigid as shown in FIG. 8. The distal drill guide 24 comprises a tapered tube 25 adapted to fit within the recess 16 in the cement 15 left by withdrawal of the prosthesis and a handle 26. After the distal drill guide is positioned within the recess 16 adjacent the blind end 21 the drill bit is inserted into the distal drill guide 24 and used to drill a hole through the blind end 21 of the cement.

The distal drill guide 24 functions not only to direct the drill bit 22 but also prevents the drill bit 22 cutting sideways into the bone 10. Especially when the prosthetic cavity 16 abuts bone 10 one one side, the drill bit 22 has a strong tendency to skive off the cement 15. The distal drill guide 24 acts to prevent lateral motion of the drill bit 22 so that the drill can be directed correctly by positioning it proximally.

As is shown in FIG. 8 a proximal drill guide 39 can be used in addition to the distal drill guide 24 to assist in the correct direction of drilling. The proximal drill guide 39 comprises a tunnel 38 through which the drill bit 22 passes and a handle 40 mounted at 90° to the longitudinal axis of the tunnel 38. The handle 40 can be calibrated as is shown schematically by lines 41. Pre-operative X-rays will determine how far laterally displaced from some fixed point the tunnel 38 needs to be and the handle 40 is then used to confirm correct displacement.

Following the drilling of the hole the saw blade 17 is then attached to a pneumatically driven reciprocating saw (partly shown at 27) and inserted into the recess 16. The saw blade 17 should be aligned in the correct plane and be inserted to the correct depth before being caused to cut into the cement 15.

Guide means 30 is then slid into the cavity. The guide means 30 (as seen in FIGS. 4 and 5) comprises a wedge 31 connected to an elongate wire handle 32. The front face of the wedge is formed with a slot 33 adapted to slide along a back edge 34 of the blade 17. The width of the wedge 31 and the depth of the slot 33 are so selected that when pushed down the prosthetic cavity to the depth indicated the distal end of the blade 17 will have been forced into the cement to the depth necessary to cut through the cement but no further.

If the saw blade 17 is too wide to fit within the recess 16 a preliminary, shallow, cut may be made with a second saw blade (not shown) to allow the insertion of saw blade 17.

Once the distal end of the cut has been made the surgeon can normally push the saw blade into the cement at the proximal end of the cavity and visually assess the correct cutting depth.

Once the cut with saw blade 17 is completed the procedure is repeated a further three times to cut the cement 15 into four segments. Each of these four segments can then be readily levered away from the femur 10 and withdrawn longitudinally from the medullary canal.

In practice it has been found that a slight cutting into the bone 10 beneath the cement 15 is acceptable. This permits the use of a pre-formed set of saw blades having shapes corresponding to internal shapes commonly found in femurs. A surgeon may select from such a preformed set the saw blade which has the best fit for each of the particular cuts which is to be made on a particular patient. It is to be understood that the use of such a preformed saw blade is encompassed within the scope of the present invention.

In another embodiment of the invention shown in FIGS. 6 and 7 the wedge 31 does not itself bear against a wall of the prosthetic cavity but rather a wedge shaped pusher 34 is provided on its own elongate handle 35 to do this. The pusher 34 includes a loop slidable on handle 32. In use after wedge 31 is positioned at the correct depth using stop 36 or handle 32 the pusher 34 is slid down the cavity and pushed wedge 31 into juxtaposition with the wall of the cavity on either side of the saw blade.

I claim:

1. A process for the removal of prosthetic cement from the medullary canal of a patient's long bone during replacement of a joint prosthesis, comprising the steps of:

a) determining the profile of a line of intersection of a plane, which extends longitudinally through the bone, the prosthetic cement and a prosthetic cavity therein, and a cement/bone interface intersected by that plane, b) determining the thickness of the prosthetic cement in said plane at least at selected points along the said bone, c) forming or selecting a substantially planar cutting blade with a cutting edge having a profile substantially corresponding to the profile of the line, d) inserting the cutting blade into the prosthetic cavity with the blade lying in said plane, the cutting edge directed towards said cement/bone interface, and to a depth such that corresponding points on the cutting edge are adjacent corresponding points on said line, e) causing the cutting blade to reciprocate, f) inserting into the prosthetic cavity between a non-cutting edge of the blade and a wall of the prosthetic cavity spaced from said cement/bone interface a guide member adapted to urge the cutting edge of the blade into the prosthetic cement towards said cement/bone interface but substantially not beyond it, g) repeating steps (e) to (f) to form at least one other cut through the prosthetic cement, and h) removing the segments of prosthetic cement so formed from medullary canal.

2. The process as claimed in claim 1 in which prior to step (d) a hole is bored in the prosthetic cement at the blind end of the prosthetic cavity.

3. The process as claimed in claim 2 in which the hole is made with a drill and a distal drill guide, the distal drill guide comprising a tapered tube adapted to fit within the prosthetic cavity adjacent the blind end thereof and around the drill when the drill is inserted into prosthetic cavity.

4. The process as claimed in claim 3 in which a proximal drill guide is provided at the proximal end of the prosthetic cavity, said proximal drill guide comprising a tunnel through which the drill passes, the tunnel being connected to a handle mounted at 90° to the longitudinal axis of said tunnel.

5. The process as claimed in claim 1 in which the guide member comprises a wedge-shaped member at the end of an elongate handle.

6. The process as claimed in claim 5 in which the wedge-shaped member has a front face and a back face, the front face being formed with a slot extending along its length parallel to the handle, the slot being such that the non-cutting edge of the blade may slidably fit into it.

7. The process as claimed in claim 6 which the total cutting depth of the blade plus the maximum thickness of the wedge-shaped member less the depth of the slot is equal to the distance from the wall of the prosthetic cavity spaced from the cement/bone interface to the cement/bone interface.

8. The process as claimed in claim 7 in which the maximum thickness of the wedge is equal to the diameter of the cavity at a point approaching the distal end of the cavity and the total cutting depth of the blade less the depth of the slot is equal to the depth of prosthetic cement at that point.

9. The process as claimed in claim 1 in which at least three cuts are formed in the prosthetic cement along three separate planes.

10. The process as claimed in claim 9 in which the cuts are substantially equiangularly spaced around the prosthetic cavity.

* * * * *